US00PP36793P2

(12) United States Plant Patent
Grazzini

(10) Patent No.: US PP36,793 P2
(45) Date of Patent: Jul. 1, 2025

(54) ***DIANTHUS* PLANT NAMED 'G22090'**

(50) Latin Name: *Dianthus hybrida*
Varietal Denomination: G22090

(71) Applicant: Garden Genetics llc, Columbus, OH (US)

(72) Inventor: Richard A. Grazzini, Columbus, OH (US)

(73) Assignee: Garden Genetics, Columbus, OH (US)

( * ) Notice: Subject to any disclaimer, the term of this patent is extended or adjusted under 35 U.S.C. 154(b) by 0 days.

(21) Appl. No.: 18/925,717

(22) Filed: Oct. 24, 2024

(51) Int. Cl.
*A01H 5/02* (2018.01)
*A01H 6/30* (2018.01)

(52) U.S. Cl.
USPC ..... Plt./273
CPC ..... *A01H 6/305* (2018.05)

(58) Field of Classification Search
USPC ..... Plt./273
CPC ..... A01H 6/305; A01H 5/02
See application file for complete search history.

*Primary Examiner* — Keith O. Robinson
(74) *Attorney, Agent, or Firm* — Cassandra Bright

(57) ABSTRACT

A new and distinct cultivar of *Dianthus* plant named 'G22090' is disclosed, characterized by large flowers with a base color of light pink with a large red-violet eye, and a very distinct star pattern in the same dark red-violet color radiating from the central eye down the petal to the petal tip. Healthy glaucous blue-green foliage exhibits good field tolerance to common *Dianthus* pathogens. The new variety is a *Dianthus*, normally used for outdoor ornamental purposes.

2 Drawing Sheets

Figure 1:
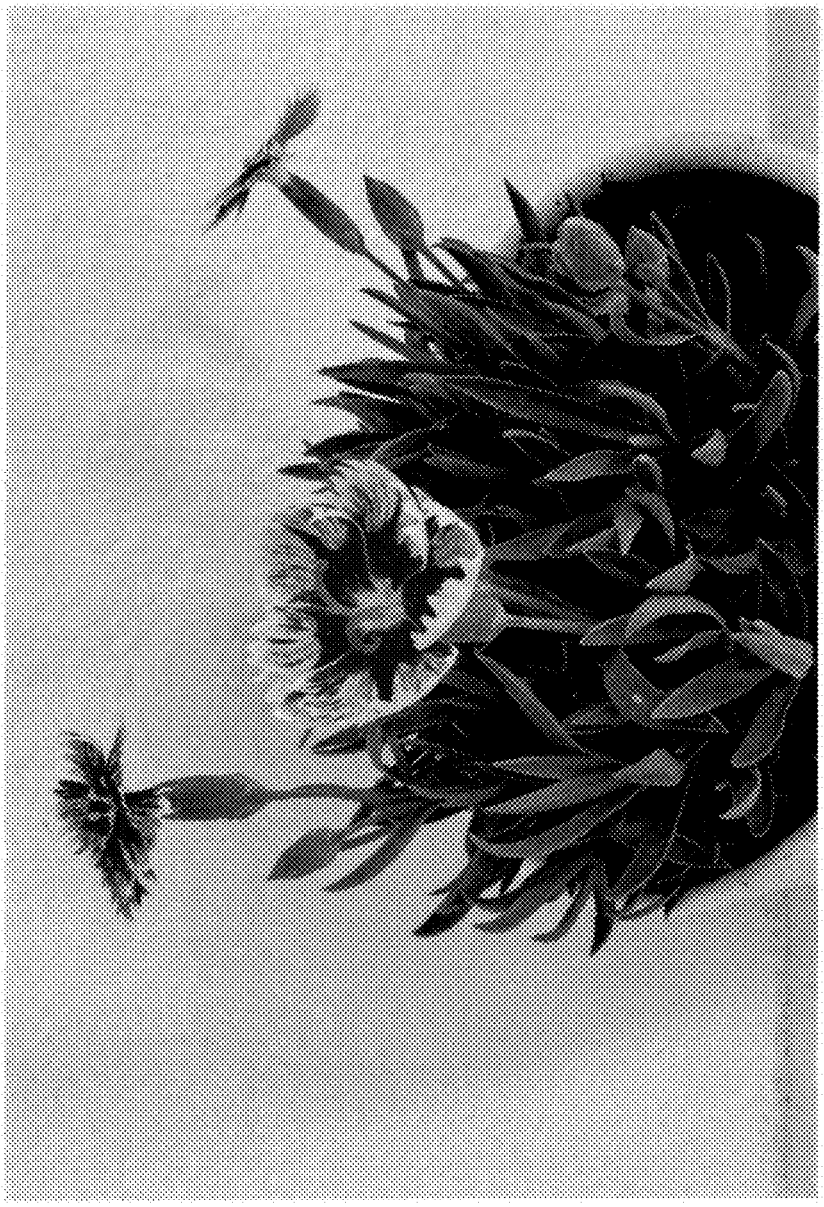

Latin name of the genus and species: *Dianthus hybrida.* Variety denomination: 'G22090'.

BACKGROUND OF THE INVENTION

The new *Dianthus* cultivar is a product of a planned breeding program conducted by the inventor at a research nursery in Bellefonte, Pennsylvania. The cross resulting in this new variety was made in May of 2020.

The seed parent is the unpatented proprietary variety referred to as *Dianthus* '50261-1'. The pollen parent is the unpatented proprietary variety referred to as *Dianthus* '50263-2'. The new variety was selected in August of 2020 by the inventor in a group of seedlings resulting from the May 2020 cross-pollination, in a nursery in Bellefonte, Pennsylvania.

Asexual reproduction of the new cultivar was performed by vegetative cuttings. This was first performed at the same nursery in Bellefonte, Pennsylvania during August of 2020, and has shown that the unique features of this cultivar are stable and reproduced true to type in multiple successive generations.

SUMMARY OF THE INVENTION

The cultivar 'G22090' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'G22090'. These characteristics in combination distinguish 'G22090' as a new and distinct *Dianthus* cultivar:

1. Large flowers.
2. Base color of flower petals is a light pink, with a large red-violet eye, and a very distinct star pattern in the same dark red-violet color radiating from the central eye down the petal to the tip.
3. Flowers have full and rounded, overlapping petals which have a diffuse red-violet blush across the petal. Petal edge is a distinct light pink to white picotee edge.
4. Spreading and dense ground-cover habit.
5. Healthy glaucous blue-green foliage.
5. Field tolerance to common *Dianthus* pathogens.
6. Strongly reblooming to constant flowering.

PARENT COMPARISONS

Plants of the new cultivar 'G22090' are similar to plants of the seed parent in most horticultural characteristics; however, plants of the new cultivar 'G22090' differ in the following:

1. Flowers of the new variety are larger than flowers of the seed parent.
2. Flowers of the new variety have a unique eye and star pattern, while flowers of the seed parent are solid colored with a dark eye.
3. Flowers of the new variety have a light pink base floret color, while flowers of the seed parent have a bright pink base color.
4. Foliage of the new variety is glaucous blue-green, while foliage of the seed parent is mid-green.
5. Plants of the new variety do not die back in the center, while plants of the seed parent show dieback.

Plants of the new cultivar 'G22090' are similar to plants of the pollen parent in most horticultural characteristics; however, plants of the new cultivar 'G22090' differ in the following:

1. Flowers of the new variety are larger than flowers of the pollen parent.

2. Flowers of the new variety have a unique eye and star pattern, while flowers of the pollen parent are solid colored with a dark eye.
3. Flowers of the new variety have a light pink base floret color, while flowers of the pollen parent have pale rose colored florets.
4. Foliage of the new variety is slightly glaucous blue-green, while foliage of the pollen parent is distinctly glaucous blue-green.
5. Plants of the new variety do not die back in the center, while plants of the pollen parent show dieback.

COMMERCIAL COMPARISONS

Plants of the new cultivar 'G22090' are comparable to the commercial variety *Dianthus* 'Kahori', unpatented. The two *Dianthus* varieties are similar in most horticultural characteristics, however, the new variety 'G22090' differs in the following:

1. Flowers of the new variety are larger than flowers of this comparator.
2. Bloom time of the new variety is extended compared to the bloom time of this comparator.
3. The new variety has healthy leaves and plant crown, while this comparator tends to develop an open crown due to plant pathogens. This comparator is also prone to develop leaf spots caused by foliar pathogens.
4. Flowers of the new variety have a unique eye and star pattern, while flowers of this comparator are rose-pink.
5. Plants of the new variety are somewhat wider than plants of this comparator.

Plants of the new cultivar 'G22090' are comparable to the commercial variety *Dianthus* 'Uribest52', U.S. Plant Pat. No. 28,239. The two *Dianthus* varieties are similar in most horticultural characteristics; however, the new variety 'G22090' differs in the following:

1. Flowers of the new variety are larger than flowers of this comparator.
2. Bloom time of the new variety is extended compared to the bloom time of this comparator.
3. Plants of the new variety are slightly taller than plants of this comparator.
4. Plants of the new variety are wider than plants of this comparator.
5. Foliage of the new variety is glaucous blue-green, while foliage of this comparator is dark green.
6. Flowers of the new variety have a unique eye and star pattern, while flowers of this comparator are bright rose-pink.

BRIEF DESCRIPTION OF THE PHOTOGRAPHS

The accompanying photograph in FIG. 1 illustrates a typical flowering plant of 'G22090' grown outdoors in Camarillo, CA at approximately 2 months old in a 1-quart pot.

Figure 2:
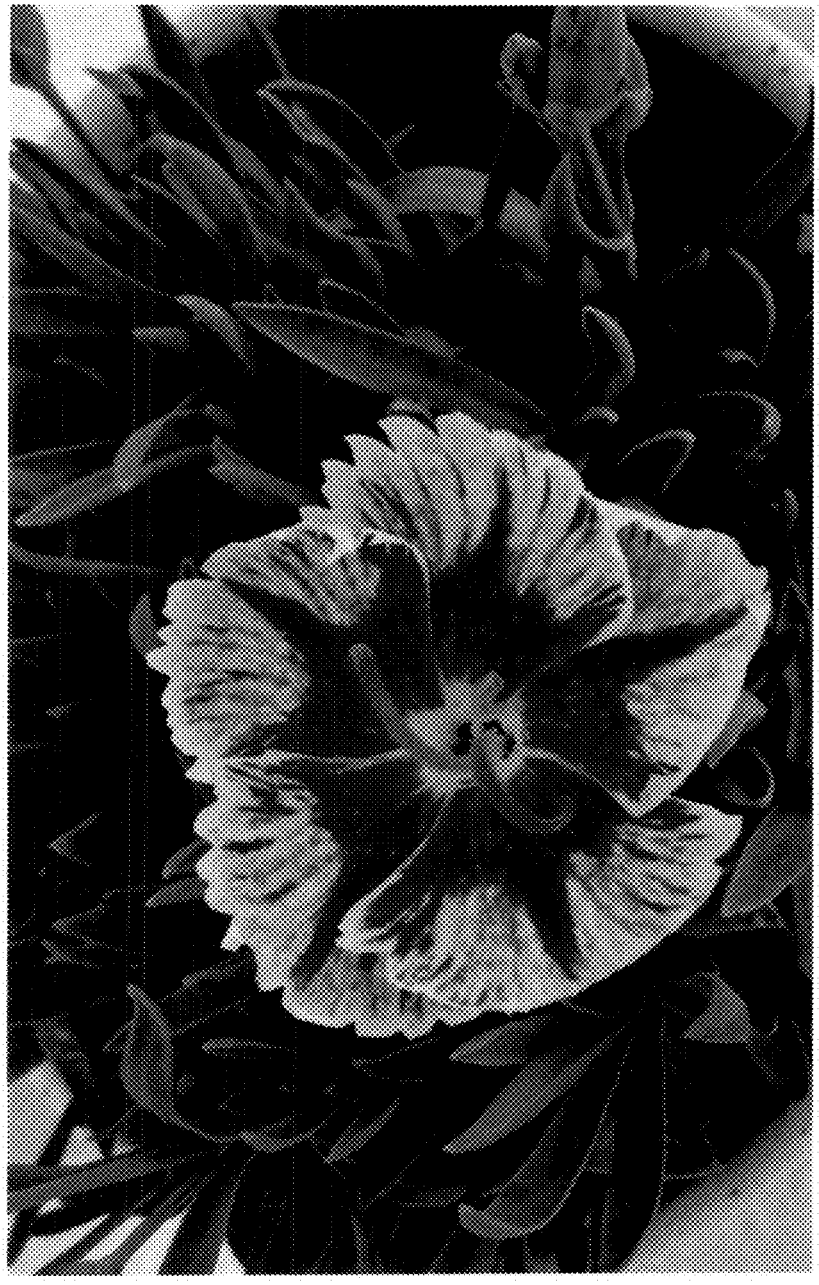

FIG. 2 illustrates a close-up view of a flower.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'G22090' plants grown outdoors in Camarillo, California. The growing temperature ranged from approximately 10° C. to 25° C. during the day and from approximately 6° C. to 12° C. during the night. General light conditions are normal sunlight and numerical values represent averages of typical plant types. Measurements were taken during June of 2021.

Botanical classification: *Dianthus hybrida* 'G22090'.

PROPAGATION

Time to initiate roots: About 10 days at approximately 24° C.

Time to produce a rooted cutting: About 18 days at 24° C.

Root description: Fibrous roots, approximately 1 to 3 mm in diameter, colored near RHS Greyed-Orange 165D.

PLANT

Age of plant described: About 10 weeks from a rooted cutting.

Container size of plant described: 1 quart.

Growth habit: Mounded flowering perennial.

Plant spread: About 24 cm.

Plant height: About 14 cm.

Plant density: Dense.

Plant vigor: Strong.

Length of plant stem: Average 9 to 12 cm.

Diameter of plant stem: Approximately 4 to 5 mm.

Quantity stems: 25 to 40.

Stem:

*Color*.—Near RHS Greyed-Green 189A, with a heavily glaucous layer of 189B.

*Texture*.—Smooth.

*Hollowness*.—Not observed on a plant of this age.

Internode length: 1.3 to 3.2 cm.

FOLIAGE

Leaf:

*Arrangement*.—Opposite (in pairs). Quantity: Approximately 8 to 12 per stem.

*Average length*.—4.1 cm.

*Average width*.—6 mm.

*Shape of blade*.—Linear.

*Curvature*.—Moderately recurved.

*Apex*.—Acute.

*Base*.—Clasping.

*Attachment*.—Sessile.

*Margin*.—Entire.

*Texture of top surface*.—Smooth.

*Texture of bottom surface*.—Smooth.

*Glaucosity*.—Medium.

*Pubescence*.—None.

*Color*.—Young foliage upper side: Near RHS Greyed-Green 191B. Young foliage under side: Near RHS Greyed-Green 1191B. Mature foliage upper side: Near RHS Greyed-Green 189A with a light glaucous layer of 191C. Mature foliage under side: Near RHS Greyed-Green 189A with a light glaucous layer of 191C.

*Venation*.—Type: Linear. Venation color upper side: Indistinguishable from foliage. Venation color under side: Indistinguishable from foliage.

FLOWER

Natural flowering season: Late Spring into Fall.
Inflorescence type and habit: Umbel of 2 to 4 single flowers, 1 to 2 flowers per stem.
Position of flower: Moderately above the foliage.
Flower longevity on plant: About 14 days.
Quantity of flowers: Approximately 12 to 20 flowers and buds on a 10-week-old plant.
Persistence: Persistent.
Fragrance: Moderate sweet to clove-like scent.
Inflorescence (umbel) size:
*Diameter*.—Approximately 5 to 7 cm.
*Height*.—Approximately 5 to 6 cm.
Individual flower size:
*Diameter*.—Approximately 3.4 cm.
*Length*.—Approximately 3 cm.
Petals:
*Arrangement*.—Single, strongly overlapping whorl.
*Shape*.—Spatulate, elongated base.
*Base*.—Long attenuate.
*Margin*.—Serrated.
*Apex*.—Serrate.
*Length*.—Upper section, outside of tube: 2 cm. Elongated base, in tube: 2.3 cm.
*Width*.—Upper section, outside of tube: 2 cm. Elongated base, in tube: 4 mm.
*Petal quantity*.—Average 5.
*Texture*.—Smooth all surfaces.
*Aspect*.—Nearly flat.
*Color*.—When opening: Upper surface: RHS Purple N79C. Large, ragged/feathered margin Red-Purple 71D, outermost margin Purple 75C. Lower surface: Near RHS Purple 75C lightly and irregularly streaked Purple 77B. Small eye Purple 75C. Fully opened: Upper surface: RHS Purple N79C, flushed Greyed-Purple N186D. Large, ragged/feathered margin Red-Purple 71D, outermost margin Purple 75D or White N155C. Small eye Purple 75D. Lower surface: Near RHS Red-Purple 73D lightly and irregularly streaked Purple 75B.
Tube:
*General description*.—Tube consists of the elongated, unfused base of the petals. Tube shape caused by a fused calyx.
*Length*.—2.1 cm.
*Width*.—4 mm.
*Texture*.—Smooth.
*Color*.—Fully opened: Inner surface: Near RHS Yellow-Green 145D, uppermost ⅓ Red-Purple 69D. Outer surface: Near RHS Yellow-Green 145D.
Bud:
*Shape*.—Elongated cylinder.
*Length*.—Average 2.8 cm.
*Diameter*.—Average 7 mm.
*Color*.—Appearing petals colored near RHS Violet 84C.
Sepals:
*Quantity*.—5.
*Arrangement*.—Fused tube.
*Shape*.—Cylindric.
*Length*.—2.1 cm.
*Width*.—5 mm.
*Margin*.—Entire.
*Apex*.—Acute.
*Texture*.—Smooth, upper and lower surfaces.
*Color*.—Near RHS Green 138B.
Bracteoles:
*Shape*.—Deltoid.
*Quantity*.—25 per flower.
*Length*.—Average 3 to 7 mm.
*Width*.—Average 3 to 5 mm.
*Margin*.—Entire.
*Texture*.—Smooth.
*Color*.—Near RHS Green 138B, base Yellow-Green 144C.
Peduncle:
*Length*.—Average 2.5 cm.
*Diameter*.—3 mm.
*Color*.—Near RHS Green 138A.
*Orientation*.—Upright.
*Strength*.—Moderate.
*Texture*.—Smooth.

REPRODUCTIVE ORGANS

Stamens:
*Number*.—About 8 to 10.
*Filament length*.—2.4 cm.
*Filament color*.—Near RHS Purple 75D.
Anthers:
*Shape*.—Linear.
*Length*.—3 mm.
*Color*.—RHS Greyed-Red 181D.
*Pollen*.—Not observed.
Pistil:
*Number*.—1, 2 stigmas.
*Length*.—2.5 cm.
*Style*.—Number: 2. Length: Approximately 1.8 cm. Color: Base near RHS Purple 75D, upper-section Red-Purple N74D.
*Stigma*.—Shape: Linear. Color: Near RHS Red-Purple N74B.
*Ovary*.—Shape: Oblong. Diameter: 3.5 mm. Length: 7 mm. Texture: Smooth. Color: Near RHS Yellow-Green 145C.

OTHER CHARACTERISTICS

Fruits and seeds: Not observed to date.
Disease/pest resistance: Shows good field-tolerance to common *Dianthus* pathogens. Common pathogens of *Dianthus* include *Pseudomonas caryophylli, Rhizoctonia solani, Fusarium oxysporum* sp. *dianthi, Fusarium roseum, Pythium* sp., *Alternaria dianthi, Verticilium dahlia* and *Verticillium alboatrum.*
Temperature range: Winter hardiness to at least USDA Zone 5.

What is claimed is:

1. A new and distinct cultivar of *Dianthus* plant named 'G22090' as herein illustrated and described.

* * * * *